United States Patent [19]

Reading et al.

[11] Patent Number: 4,927,761

[45] Date of Patent: May 22, 1990

[54] IMMOBILIZATION OF CELLS WITH ALGINATE AND AGAROSE

[75] Inventors: Anthony H. Reading, Wantage; Brynley J. Miles, Cirencester, both of United Kingdom

[73] Assignee: The Secretary of State for United Kingdom Atomic Energy Authority in Her Britannic Majesty's Government of the United Kingdom of Great Britain and Northern Ireland, London, England

[21] Appl. No.: 162,579

[22] Filed: Mar. 1, 1988

[30] Foreign Application Priority Data

Mar. 9, 1987 [GB] United Kingdom ................. 8705464

[51] Int. Cl.$^5$ ...................... C12N 11/10; C12N 11/02; C12N 5/02
[52] U.S. Cl. .................................... 435/178; 435/177; 435/240.22
[58] Field of Search ............... 435/174, 176, 177, 178, 435/179, 180, 182, 240.22

[56] References Cited

U.S. PATENT DOCUMENTS 4,352,883 10/1982 Lim .................................. 435/182 X
4,572,897 2/1986 Amotz et al. ....................... 435/177

OTHER PUBLICATIONS

Mattiasson, Bo, Immobilized Cells and Organelles, vol. I, CRC Press, Floria, 1983, pp. 8-19 and 31-35.

Primary Examiner—David M. Naff
Attorney, Agent, or Firm—Larson and Taylor

[57] ABSTRACT

Biological cells are immobilized by forming a mixture of the cells and a first and second gel component, gelling the mixture with a gelling reagent and removing at least a portion of the first component to leave a gel containing the second component and the cells. Preferably, the first and second gel components are alginate and agarose, respectively, and the gelling reagent is calcium chloride.

5 Claims, No Drawings

IMMOBILIZATION OF CELLS WITH ALGINATE AND AGAROSE

The present invention relates to composite materials and more particularly to composite materials containing a selected substance.

It is known to use a gel component as a support for a substance such as, for example, biological cells. It is often desirable to form the gel component containing the substance into a chosen physical form such as beads. A problem arises in that it can prove impossible to find a gel component which has all the properties required for fabrication of gel material containing the substance and which will also function satisfactorily in subsequent use.

For example, if biological cells are immobilised in an alginate gel alone difficulties may be encountered due to the nature of the gel being such that free diffusion of species (e.g. product species such as antibodies) may be inhibited; some types of alginates are unstable and tend to dissolve in nutrient medium used to maintain the cells.

The immobilisation of cells in an agarose gel alone may suffer from difficulties also in that it may be difficult to form beads on a large scale (say greater than 1 liter) due to the relatively long setting time of agarose.

We have found that it is possible to overcome problems of this type by combining two (or more) gel components in the fabrication stage and subsequently removing one (or some) of the gel components.

According to one aspect of the present invention there is provided a method for preparing a composite material containing a selected substance which method comprises forming a gel material said gel material containing a selected substance, a first gel component and a second gel component, and removing at least a proportion of the first gel component to leave a composite material comprising a selected substance retained in a gel comprising the second gel component.

In one embodiment of the present invention there is provided a method for preparing a composite material containing immobilised cells which method comprises forming a gel material said gel material containing cells, a first gel component and a second gel component, and removing at least a proportion of the first gel component to leave a composite material comprising cells retained in a gel comprising the second gel component.

It is to be understood that the gel components may be themselves gels as such (i.e. it is not necessary for the two gel components to be dependent upon each other for gel formation); thus the composite material may comprise cells and two or more gel components each of which gel component is in itself an independent gel.

It is to be further understood that, by way of example, if desired, the removal of the first gel component may be such as to leave a composite material comprising a selected substance retained in a gel comprising essentially the second gel component.

By way of example, a method in accordance with the present invention for preparing a composite material containing immobilised cells comprises forming a mixture of cells, a precursor for a first gel component and a precursor for a second gel component, causing the precursor for the first gel component to gel to form a first gel component, causing the precursor for the second gel component to gel to form a second gel component, and subsequently removing at least a proportion of the first gel component to leave a composite material comprising cells retained in a gel comprising the second gel component.

It is to be understood that the precursor for the first gel component may be such that it can be caused to form a first gel component relatively more quickly than the precursor for the second gel component can be caused to form the said second gel component.

Thus, the second gel component may be, for example, a hydrophilic monomer or polymer which forms a gel component relatively slowly (e.g. by polymerising or cross-linking).

The first gel component may be, for example, formed by gelling an alginate (e.g. by contacting alginic acid with a calcium chloride solution).

By way of example, the second gel component may be formed from agarose or carrageenan gum.

The cells may be by way of example biological cells (e.g. eukaryotic cells such as animal cells and plant cells, or prokaryotic cells such as microbial cells).

By way of example, in a method in accordance with the invention a mixture of cells, a precursor for a first gel component and a precursor for a second gel component are formed into droplets and the droplets treated to cause the precursor for the first gel component to gel and to cause the precursor for the second gel component to gel, and subsequently at least a proportion of the first gel component is removed to leave a particulate composite material comprising particles of gel containing cells.

For example, the droplets may be contacted with a reagent (e.g. by allowing the droplets to fall into a vessel containing a reagent) capable of causing the precursor for one of the gel components to gel.

Particulate composite material in accordance with the present invention may be incorporated in a biochemical reactor.

In accordance with one particular example of the present invention a mixture is formed containing cells, alginate and agarose, the mixture is formed into droplets and contacted with a reagent to gel the alginate, thereby to provide a stable matrix within which the agarose is held until set, and subsequently alginate is removed to leave beads of porous agarose gel containing immobilised cells.

Calcium chloride may be used to gel the alginate.

The agarose used may be, for example, one with a low gelling temperature such that it is not necessary to keep cells at unnecessarily elevated temperatures for substantial lengths of time.

The present invention will now be further described, by way of example only, as follows:

EXAMPLE 1

A solution of composition 2% sodium alginate (Sigma Type VI alginate) and 2% agarose (Park Scientific LSL agarose) in phosphate buffered saline was sterilized by autoclaving at 121° C. for 15 minutes and was then allowed to cool to 45° C.

All subsequent operations were performed aseptically.

Hybridoma cells were harvested from a suspension culture and resuspended in 10 ml of nutrient medium type RPMI 1640 supplemented with 5% foetal calf serum, 2 mM glutamine, 50 IU/ml penicillin and 50 ug/ml streptomycin to give a final concentration of $1.8 \times 10^7$ cells/ml with a viability of 88%, as assessed by trypan blue dye exclusion.

[The concentration of 5% of foetal calf serum is not a critical value and concentrations down to 0.75% have been used.]

The 10 ml volume of cell suspension thus prepared was warmed to 45° C. and mixed with an equal volume of the agarose/alginate solution and the resulting mixture then formed into droplets using a droplet generator. The liquid droplets were contacted with a solution of $CaCl_2$, (50 mM) and NaCl (79 mM) (pH 7.3 at 25° C.).

The resulting beads were transferred to an aqueous solution of trisodium citrate (50mM) and NaCl (54 mM) (pH 7.3) for 10 minutes and then washed with 200 ml of phosphate buffered saline to remove alginate.

The resulting beads were collected and transferred to RPMI type nutrient medium. The cells trapped within the beads were found to have a post immobilization viability of at least 70% as assessed by a fluorescein diacetate/propidium iodide staining technique.

Cell viability within the beads was assessed at greater than 60% after 3 weeks of maintenance in this type of nutrient medium.

Beads formed by the method of Example 1 show permeability to molecules in excess of 2,000,000 molecular weight. This was determined by co-immobilisation of the agarose/alginate gel with Blue Dextran (molecular weight 2,000,000). On removal of the alginate from the composite (using sodium citrate), the Blue Dextran was found to diffuse out of the beads very rapidly to reach equilibrium with the surrounding solution.

EXAMPLE 2

The procedure of Example 1 was repeated using 2% British Drug House sodium alginate and 2% Park Scientific LSL agarose. Essentially similar cell viability results were obtained.

EXAMPLE 3

The procedure of Example 1 was repeated with the following changes:
(1) a 2% FMC Seaplaque agarose was used having a gelling temperature in the range 26° C. to 30° C.;
(2) after sterilising, the mixed alginate, agarose solution was allowed to cool to 37° C.;
(3) the cell suspension was formed and maintained at 37° C. (rather than having to be heated to 45° C.).

The post immobilisation viability in this example was found to be 70%. The lower temperature used during immobilisation is more readily tolerated by the cells, but does carry the disadvantage of a reduced gel strength. However, this can be accepted given careful reactor design to ensure mild agitation of the beads in reactor operation.

We claim:

1. A method for preparing a composite material containing immobilized viable biological cells, said method comprising forming a mixture consisting essentially of viable biological cells, alginate and agarose; forming droplets of said mixture; contacting said droplets with a reagent to gel the alginate to thereby provide a stable matrix within which the agarose is held until set, said matrix containing said viable biological cells; and subsequently removing at least a portion of said alignate to form a composite material comprising beads of porous agarose gel in which said viable biological cells are immobilized.

2. A method as claimed in claim 1, wherein said viable biological cells comprise eukaryotic cells.

3. A method as claimed in claim 1, wherein said viable biological cells comprise prokaryotic cells.

4. A method as claimed in claim 1, wherein the droplets are contacted with the reagent by allowing them to fall into a vessel containing the reagent.

5. A method as claimed in claim 1, wherein said reagent comprises calcium chloride.

* * * * *